United States Patent
Haase et al.

(10) Patent No.: US 11,839,457 B2
(45) Date of Patent: Dec. 12, 2023

(54) MEASUREMENT GUIDANCE FOR CORONARY FLOW ESTIMATION FROM BERNOULLI'S PRINCIPLE

(71) Applicant: KONINKLIJKE PHILIPS N.V., Eindhoven (NL)

(72) Inventors: Christian Haase, Hamburg (DE); Michael Grass, Buchholz in der Nordheide (DE); Arjen Van Der Horst, Tilburg (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 310 days.

(21) Appl. No.: 16/764,055

(22) PCT Filed: Nov. 16, 2018

(86) PCT No.: PCT/EP2018/081484
§ 371 (c)(1),
(2) Date: May 14, 2020

(87) PCT Pub. No.: WO2019/101630
PCT Pub. Date: May 31, 2019

(65) Prior Publication Data
US 2020/0390345 A1    Dec. 17, 2020

(30) Foreign Application Priority Data

Nov. 23, 2017   (EP) .................................... 17203207

(51) Int. Cl.
*A61B 5/0285* (2006.01)
*A61B 34/10* (2016.01)
(Continued)

(52) U.S. Cl.
CPC .......... *A61B 5/0285* (2013.01); *A61B 5/0215* (2013.01); *A61B 34/10* (2016.02);
(Continued)

(58) Field of Classification Search
CPC ... A61B 5/02007; A61B 5/0215; A61B 5/026; A61B 5/0285; A61B 6/032; A61B 6/487;
(Continued)

(56) References Cited

U.S. PATENT DOCUMENTS 6,354,999 B1 * 3/2002 Dgany ................... A61B 1/015
                                                   600/561
10,945,613 B2 * 3/2021 Kramer .................. A61B 5/026
(Continued)

FOREIGN PATENT DOCUMENTS

EP      2633815 A1    9/2013
WO      200053081 A1   9/2000
(Continued)

OTHER PUBLICATIONS

Li et al. "Impact of side branch modeling on computation of endothelial shear stress in coronary artery disease: coronary tree reconstruction by fusion of 3D angiography and OCT." Journal of the American College of Cardiology 66.2 (2015): 125-135. (Year: 2015).*

(Continued)

*Primary Examiner* — Katrina R Fujita

(57) ABSTRACT

An apparatus for assessing a hemodynamic property in a coronary vasculature and a corresponding method are provided in which diagnostic data of a vessel of interest is used to identify a first and second measurement position at which a first and a second value for a first hemodynamic property may be obtained whereby these first and second values are suitable to derive at least one diagnostic parameter indicative of a second hemodynamic 5 property that cannot or should not be measured directly.

14 Claims, 4 Drawing Sheets

(51) Int. Cl.
  *G06T 7/11* (2017.01)
  *G16H 50/50* (2018.01)
  *G16H 50/30* (2018.01)
  *G16H 50/20* (2018.01)
  *G16H 30/40* (2018.01)
  *A61B 5/0215* (2006.01)
  *G06T 7/60* (2017.01)

(52) U.S. Cl.
  CPC ............... *G06T 7/11* (2017.01); *G06T 7/60* (2013.01); *G16H 30/40* (2018.01); *G16H 50/20* (2018.01); *G16H 50/30* (2018.01); *G16H 50/50* (2018.01); *A61B 2034/105* (2016.02); *G06T 2207/30101* (2013.01)

(58) Field of Classification Search
  CPC ....... A61B 6/504; A61B 6/507; A61B 6/5217; A61B 34/10; A61B 2034/105; G16H 30/40; G16H 50/20; G16H 50/30; G16H 50/50; G06T 7/11; G06T 7/60; G06T 2207/30101
  See application file for complete search history.

(56) References Cited

U.S. PATENT DOCUMENTS

| | | | |
|---|---|---|---|
| 2014/0024932 A1 | 1/2014 | Sharma | |
| 2014/0066765 A1* | 3/2014 | Fan | A61B 8/0891 600/407 |
| 2014/0073976 A1* | 3/2014 | Fonte | A61B 6/5217 600/504 |
| 2014/0121513 A1* | 5/2014 | Tolkowsky | G16H 50/30 600/431 |
| 2015/0324962 A1 | 11/2015 | Itu | |
| 2015/0374243 A1* | 12/2015 | Itu | A61B 5/7275 703/2 |
| 2016/0058407 A1* | 3/2016 | Wakai | A61B 5/055 600/407 |
| 2016/0117816 A1 | 4/2016 | Taylor | |
| 2016/0157787 A1 | 6/2016 | Merritt | |
| 2016/0302750 A1* | 10/2016 | Nickisch | A61B 6/5217 |
| 2017/0281018 A1* | 10/2017 | Kramer | G16H 50/50 |
| 2017/0286628 A1* | 10/2017 | Shim | G16H 30/40 |
| 2017/0325770 A1* | 11/2017 | Edic | A61B 6/503 |
| 2018/0206808 A1* | 7/2018 | Grass | G06T 7/0016 |
| 2018/0344173 A1* | 12/2018 | Tu | A61B 5/02007 |

FOREIGN PATENT DOCUMENTS

| | | |
|---|---|---|
| WO | 200113779 A2 | 3/2001 |
| WO | 2016159881 A1 | 10/2016 |
| WO | 2017021201 A1 | 2/2017 |
| WO | 2017055228 A1 | 4/2017 |

OTHER PUBLICATIONS

Tu et al. "Fractional flow reserve calculation from 3-dimensional quantitative coronary angiography and TIMI frame count: a fast computer model to quantify the functional significance of moderately obstructed coronary arteries." JACC: Cardiovascular Interventions 7.7 (2014): 768-777. (Year: 2014).*

Van der Horst, et al. "Towards patient-specific modeling of coronary hemodynamics in healthy and diseased state." Computational and mathematical methods in medicine 2013 (2013). (Year: 2013).*

International Search Report & Written Opinion of PCT/EP2018/081484, dated Feb. 4, 2019.

Ogerfo, Frank W. et al "Effect of Flow Split on Separation and Stagnation in a Model Vascular Bifuration", Stroke, vol. 12, No. 5, 1981.

Van De Hoef, Tim P. et al "Fractional Flow Reserve as a Surrogate for Inducible Myocardial Ischaemia", Nature Reviews/Cardiology, vol. 10, Aug. 2013.

* cited by examiner

MEASUREMENT GUIDANCE FOR CORONARY FLOW ESTIMATION FROM BERNOULLI'S PRINCIPLE

CROSS-REFERENCE TO PRIOR APPLICATIONS

This application is the U.S. National Phase application under 35 U.S.C. § 371 of International Application No. PCT/EP2018/081484, filed on Nov. 16, 2018, which claims the benefit of European Patent Application No. 17203207.0, filed on Nov. 23, 2017. These applications are hereby incorporated by reference herein.

FIELD OF THE INVENTION

The present invention relates to an apparatus for assessing a hemodynamic property in a coronary vasculature, a corresponding method and a respective computer program. In particular, the present invention relates to improved measurement guidance for performing measurements of hemodynamic parameters by deriving optimal measurement positions for intravascular measurements from diagnostic data of the vasculature.

BACKGROUND OF THE INVENTION

Functional stenosis severity in coronary arteries may typically be assessed by means of intravascular pressure measurements. In that regard, assessment may particularly be performed by considering the ratio of the pressure distal the stenosis ($P_d$) to the pressure in the aorta ($P_a$). Hereby, this ratio may be regarded using indices such as Fractional Flow Reserve (FFR) or instantaneous wave-Free Ratio (iFR), both of which are determined from said pressure ratio. FFR measurements use whole-cardiac cycle pressure traces and have to be performed in a state of hyperemia, typically induced by the administration of vasodilatory agents. In contrast, iFR measurements are performed at rest during a specific period of the cardiac cycle, namely the diastole, which is also referred to as the wave-free period.

While pressure-based indices allow for a sufficient understanding of the coronary artery lesions, an additional measurement of the flow properties of the blood might provide additional insights enabling a more thorough diagnosis of the coronary vasculature and, accordingly, an improved treatment planning of the coronary artery lesions present therein. To that end, the measurement of flow velocity and/or volumetric flow rate through a vessel of interest in the vasculature may be particularly suitable to improve the understanding of the coronary lesions.

Another important index to correctly assess lesions in the coronary arteries is the so-called Coronary Flow Reserve (CFR), which defines the maximum increase in blood flow through the vasculature above the normal resting volume. The CFR may be obtained by a measurement of the ratio between hyperemic and resting flow.

Despite these benefits, routine flow measurements in order to assess further hemodynamic properties have not found its way into clinical practice, due to the added complexity and the lack of robustness of any measurement techniques available for measuring flow-related parameters.

EP 2 633 815 A1 discloses approaches for assessing hemodynamic characteristics for an organ of interest. In one implementation, a fluid dynamics model may be provided with data derived from an anatomic imaging modality and blood flow information derived by ultrasound to derive the desired hemodynamic characteristics. In one such implementation, a fractional flow reserve is estimated.

WO 2017/021201 A1 discloses an assistance device, an assistance system and an assistance method for assisting a practitioner in an interventional hemodynamic (e.g fractional flow reserve (FFR)) measurement on a subject. The FFR pressure measurements are combined with an angiography-based assessment of the coronary vessel geometry. An advanced computational fluid dynamics model may be employed to add flow and myocardial resistance data based on the interventional pressure values and on a vascular model generated prior to the intervention. In case that these data are available prior to the intervention, the location of most optimal positions for pressure measurements can be pre-calculated and by overlay of the vessel tree, for example, on the X-ray projection, advice can be given for the interventional cardiologist during the intervention.

SUMMARY OF THE INVENTION

Instead of measuring flow properties, such as flow velocity and volumetric flow rate, directly, these properties may be approximated from pressure measurements according to Bernoulli's principle. However, in order to obtain a sufficiently accurate approximation, the pressure measurements have to be performed at suitable measurement positions inside the vessel of interest in the vasculature.

It is therefore an object of the present invention to provide an improved apparatus which allows for assessing a hemodynamic property, such as a flow property, inside a vessel of interest in a patient's vasculature.

It is a further object of the invention to provide an improved method for deriving diagnostic parameters indicative of hemodynamic properties, such as flow properties, from measurements of other hemodynamic properties, such as pressure measurements. Even more particularly, it is an object of the present invention to provide an apparatus for assessing and modeling the coronary physiology on the basis of diagnostic data of the vasculature with which a diagnostic parameter such as CFR may be determined with high accuracy.

Therefore, an apparatus for assessing a coronary vasculature is provided, the apparatus comprising an input unit for receiving diagnostic data of a vessel of interest in the vasculature and an identification unit for identifying, using the diagnostic data, a first intravascular measurement position, wherein a first hemodynamic value of a first hemodynamic property is derived at said first intravascular measurement position, and a second intravascular measurement position, wherein a second hemodynamic value of the first hemodynamic property is derived at said second intravascular measurement position. The apparatus further comprises a computation unit for computing, on the basis of the first hemodynamic value and the second hemodynamic value, at least one diagnostic parameter representative of a second hemodynamic property in the vessel of interest.

Hereby, the term vessel of interest may particularly refer to a vessel or vessel tree in the patient's coronary vasculature. Even more particularly, the term vessel of interest may refer to one or more vessel segments of the vessel of interest in the patient's vasculature. Also, it shall be understood that the term (first or second) hemodynamic property may generally refer to any property representative of the hemodynamics inside the patient's vasculature. Further, the term hemodynamic value may refer to a measurement value of a hemodynamic property of the vasculature, whereby the hemodynamic value is acquired by a measurement at a particular intravascular position along a longitudinal axis of the vessel of interest.

In some embodiments, the hemodynamic properties may relate to properties such as vessel wall friction, vessel wall elasticity, vessel impedance, blood viscosity, blood pressure, flow velocity volumetric flow rate, volumetric outflow rate through vessel bifurcations or the like. In this context, a first and a second hemodynamic value may particularly be derived for a first hemodynamic property, such as the pressure inside the vessel of interest and, subsequently, be used to compute a diagnostic parameter that represents a second hemodynamic property, such as the volumetric flow rate. Hence, a first hemodynamic property may be used to derive a second hemodynamic property, different from the first hemodynamic property.

The term diagnostic data may refer to any kind of measurement data representative of the vasculature including the vessel of interest. More particularly, diagnostic data may comprise diagnostic image data acquired by an imaging modality, such as X-ray scanning, computed tomography (CT), X-ray angiography, positron emission tomography (PET), single photon emission computed tomography (SPECT), ultrasound imaging, or the like. The diagnostic image data may hereby comprise a single two-dimensional or three-dimensional diagnostic image or a time series of diagnostic images collected over a certain time span. The diagnostic image data may relate to perfusion data obtained using magnetic resonance imaging (MRI), CT and/or PET.

The diagnostic data may further comprise measurement data acquired by an intravascular measurement that has been performed in-situ, i.e. from inside the vessel of interest. To that end, the diagnostic data may comprise intravascular image data that has been acquired using an intravascular imaging modality, such as intravascular ultrasound (IVUS) and/or optical coherence tomography (OCT), obtained by a measurement device attached to a catheter that is introduced into the vessel of interest. The intravascular image data may comprise a single intravascular image or a time series of intravascular images collected for the same intravascular measurement position over time. Additionally or alternatively, the intravascular image data may also be collected by slowly pulling back the catheter through the vessel and by obtaining a plurality of intravascular images at a plurality of intravascular measurement positions.

The diagnostic data may also comprise intravascular measurement data acquired during an intravascular measurement. This intravascular measurement data may particularly refer to pullback data. The term pullback data generally relates to a plurality of hemodynamic values determined at a plurality of intravascular positions along the longitudinal axis of a vessel of interest. Pullback data is obtained for a particular pullback length, which is defined as the distance between the starting position of the determination of the plurality of hemodynamic values and the ending position of this determination. The pullback data may for example be used to determine a pressure gradient along the vessel of interest, i.e. may be used to determine a plurality of pressure values for the plurality of intravascular positions, typically starting at a distal position and ending at a proximal position. In that context, the terms proximal and distal shall be understood within their conventional meaning, i.e. as defining a position close and a position distant from the main mass of the body, respectively. In terms of coronary vessels, a proximal position is a position closer to the heart and a distal position relates to a position more distant from the heart compared to the proximal position when viewed along a longitudinal axis of the coronary vessel.

The term measurement position may generally refer to an intravascular position at which the hemodynamic value of the first hemodynamic property may be measured. It shall be understood that this measurement of the first hemodynamic property may be performed as part of the diagnostic data acquisition, e.g. in case the diagnostic data comprises (pressure) pullback data. Alternatively or additionally, the measurement of the first hemodynamic property may be performed in a further measurement step following the identification of the first and second measurement position using the diagnostic data.

Hence, in the first case, the deriving of the first and second hemodynamic value at the first and second measurement position particularly refers to determining, from the already acquired diagnostic data, the first and second hemodynamic value as measured at the identified first and second measurement position. In contrast to that, in the second case, the deriving of the first and second hemodynamic value refers to a situation where the first and second measurement position are identified from the diagnostic data and, subsequently, an (intravascular) measurement of the first hemodynamic property is performed at the first and second measurement position to measure the first and second hemodynamic value. Details of these different approaches will be described herein below in relation to the various embodiments.

Using diagnostic data to identify the first and second measurement position allows to determine the optimum measurement positions for acquiring measurement values of the first hemodynamic property, whereby the values acquired at these positions allow for an improved approximation, i.e. computing, of a second hemodynamic property.

In some embodiments, the first hemodynamic property comprises a pressure in the vessel of interest. Accordingly, the hemodynamic value derived for the first hemodynamic property is an intravascular pressure value. As outlined above, pressure values are particularly suited for deriving further hemodynamic properties, such as flow properties. More particularly, blood flow properties may be derived from measured pressure values according to Bernoulli's principle.

Bernoulli's principle particularly relates pressure to flow velocity, defining that an increase in flow velocity of an incompressible fluid (like human or animal blood) occurs simultaneously with a decrease in pressure. If friction losses and changes in the fluid's potential energy are neglected, a local change in flow velocity v between a first measurement position (1) and a second measurement position (2) defines a change in pressure p between these positions as $$\Delta p = p_1 - p_2 = \rho/2(v_2^2 - v_1^1),$$

where $\rho$ is the density of the fluid.

Further, the volumetric flow rate Q in the vessel of interest may generally be determined as $$Q = vA,$$

where A is the cross sectional (vessel) area at a particular position of the vessel of interest (i.e. in a particular vessel segment) and v is the flow velocity through said vessel of interest. In case of lesions and/or narrowings in the vessel the cross sectional area A is changed. If the volumetric flow rate Q may be assumed to be constant along the length of the vessel segment to be regarded, due to the lack of bifurcations through which an outflow from the vessel of interest may occur in the respective vessel segment, a change in the cross sectional area A results in a change of the local flow velocity along the considered vessel segment. Accordingly, the volumetric flow rate Q may be assumed to be equal at the first measurement position (1) and the second measurement position (2) in the vessel segment:

$$Q = v_1 A_1 = v_2 A_2.$$

As such, by means of measuring the pressure difference $\Delta p = p_1 - p_2$ between the first measurement position (1) and the second measurement position (2) and determining the local cross sectional areas $A_1$ and $A_2$, the volumetric flow rate may be computed using a calculation according to $$Q = A_1 A_2 \sqrt{\frac{2}{\rho} \cdot \frac{(p_1 - p_2)}{A_1^2 - A_2^2}}.$$

A flow ratio like the Coronary Flow Reserve (CFR), which corresponds to the ratio of the volumetric flow rate under hyperemic ($Q_H$) and resting ($Q_R$) conditions may thus be derived according to $$CFR = \frac{Q_H = A_1 A_2 \sqrt{\frac{2}{\rho} \cdot \frac{\Delta p_H}{A_1^2 - A_2^2}}}{Q_R = A_1 A_2 \sqrt{\frac{2}{\rho} \cdot \frac{\Delta p_R}{A_1^2 - A_2^2}}} = \sqrt{\frac{\Delta p_H}{\Delta p_R}}.$$

It shall be understood that, in this case, the pressure values have to be obtained at the first and second measurement position for both, the hyperemic as well as the resting state, respectively.

Thus, flow-related hemodynamic properties may potentially be derived from a pressure measurements performed at least two measurement positions. In order to derive accurate parameters for the flow-related hemodynamic properties, though, the pressure measurements may not be performed at two arbitrary positions. Rather, it has to be ensured that the flow velocities—and, therefore, the pressure values—at the first and second measurement position differ significantly from one another, such that the pressure difference $\Delta p = p_1 - p_2$ may be measured sufficiently well, even in case the pressure probe for measuring the pressure values has a limited accuracy.

To that end, in some embodiments, the identifying the first intravascular measurement position and the second intravascular measurement position comprises predicting a localized change in the second hemodynamic property in the vessel of interest at least one candidate position, identifying said at least one candidate position as the first intravascular measurement position and identifying an intravascular position other than the at least one candidate position as the second intravascular measurement position.

As indicated herein above, a flow property may be from pressure values obtained at a first and a second measurement position at which the pressure shows a significant difference. While these first and second measurement positions may typically be found in a particular vessel, or segment thereof, their identification is not straightforward. In some embodiments, the first and second measurement positions are thus identified on the basis of the diagnostic data.

This may particularly be achieved by predicting, on the basis of the diagnostic data, a localized change in the second hemodynamic property. In some embodiments, this second hemodynamic property may particularly relate to the flow velocity and the diagnostic data may be used to anticipate an increase or a decrease in the local flow velocity at a particular position along the longitudinal axis in the vessel of interest.

The predicting may be performed in a variety of manners, depending on the kind of diagnostic data used. In case of diagnostic image data and/or intravascular image data obtained by a respective imaging modality, the predicting may particularly be performed by detecting, in the image data, a local change in the cross sectional area of the vessel of interest, e.g. due to a lesion and/or narrowing in the vessel of interest. As already mentioned, since the volumetric flow rate should be constant throughout the vessel, when not considering any outflow from the vessel, a change of the cross sectional area of the vessel indicates a change in the flow velocity, since the same volume of blood has to pass a different cross sectional area. Hence, from the image data it may be predicted that, at a position of a lesion and/or a narrowing, the flow velocity, as the second hemodynamic property, will show a localized change, i.e. an increase or a decrease in value.

In case of pullback data comprising a plurality of hemodynamic values of a first hemodynamic property, the hemodynamic values may be used to predict changes in the values of the second hemodynamic property. As previously mentioned, the different hemodynamic properties are related to one another according to fluid dynamic laws. Hence, it is possible to derive, from pullback data which provides a plurality of values for the first hemodynamic property, at least one diagnostic parameter indicative of the second hemodynamic property.

In some embodiments, the pullback data may particularly comprise a plurality of pressure values acquired at a plurality of positions along the longitudinal axis of the vessel of interest starting at a distal position and ending at a proximal position. Accordingly, the first hemodynamic property may be related to the pressure inside the vessel of interest. The second hemodynamic property in this case may particularly be the flow velocity. As indicated herein above, the pressure and the flow velocity are related via Bernoulli's law and, thus, a change in the local flow velocity will also result in a change in pressure. Hence, by regarding a pressure pullback curve comprising a plurality of pressure values, local pressure changes, in particular local pressure decreases, may be identified. At the position of such a local pressure change, a change in flow velocity may be predicted.

As such, in both cases, image data as well as pullback data, ultimately a change in flow velocity at a particular position may be predicted.

The position of said change in flow velocity may then be identified as a candidate position for the first measurement position, i.e. a position at which a first hemodynamic value may be determined which differs significantly from a second hemodynamic value measured at a second measurement position. In order to ensure such difference, the second measurement position is typically identified as a further intravascular position which is assumed to not be affected by the narrowing and/or lesion. Accordingly, the further intravascular position should be located far enough away from the narrowing and/or lesion so that no turbulences caused by the narrowing and/or lesion remains, while at the same time not being located too far away from the narrowing and/or lesion such that side effects such as friction losses and outflow to minor vessels become too significant to be neglected in the approximation.

The further intravascular position may thus be considered an additional position inside the vessel at which the measurement of the second hemodynamic value may be performed, such that the second hemodynamic value differs significantly from the first hemodynamic value. This additional intravascular position may hereby be located proximal or distal to the candidate position.

In some embodiments, both, the first and the second measurement position may particularly be defined by the narrowing and/or lesion, with the candidate position identified as the first measurement position being located at the position of the narrowing and/or lesion, i.e. inside the narrowing and/or lesion, and the further intravascular position designated the second measurement position being positioned further away from it along the longitudinal axis of the vessel of interest. In some embodiments, the further intravascular position, in order to qualify as a suitable second measurement position, may particularly be distanced from the candidate position identified as the first measurement position by about 0.5 to 2 cm, more specifically 1 cm, along the longitudinal axis of the vessel of interest. Even more particularly, the further intravascular position may be located 1 cm proximal or distal from the narrowing and/or lesion and, thus, from the candidate position designated as the first measurement position.

Alternatively or additionally, the identification of the second measurement position may also be performed using further and/or different criteria. In some embodiments, a healthy looking vessel segment of the vessel of interest may be identified using respective diagnostic image data and/or intravascular image data. To that end, the term healthy particularly refers to the vessel segment not exhibiting any narrowing and/or lesions. The further intravascular measurement position may be located in this healthy looking vessel segment and, due to being located herein, be identified as the second measurement position.

In some embodiments, in which the diagnostic data comprises pullback data, the pullback curve resulting from the pullback data may be regarded. If the pullback curve exhibits a constituent slope along a plurality of intravascular positions, this may be assumed as indicating a healthy vessel segment. An intravascular position located in the vessel segment may then be identified as the second measurement position.

Alternatively and or additionally, the identification of the second measurement position may be performed at least partially based on the presence and/or absence of bifurcations between the candidate position and the further intravascular position. More specifically, a further intravascular position may be identified as a second measurement position if there are no bifurcations present between the candidate position identified as the first measurement position and itself and may not be identified as the second measurement position if bifurcations are present in between the candidate position and the further intravascular measurement position.

By identifying the first and second measurement position in this manner, it may be ensured that the first and second hemodynamic value obtained at these positions differ significantly from one another. More specifically, choosing the first and second measurement position in this manner may allow to approximate the diagnostic parameter indicating the second hemodynamic property in spite of possible measurement accuracies.

In some embodiments, the diagnostic data comprises at least one diagnostic image of the vessel of interest. Hereby, the identifying of the first intravascular measurement position and the second intravascular measurement position comprises segmenting the vessel of interest into a plurality of segments, deriving, for each of the segments, a plurality of geometric parameter values for the vessel of interest at a plurality of intravascular positions along a longitudinal axis of the vessel of interest and identifying, from the plurality of geometric parameter values at the plurality of intravascular positions, at least one geometric parameter value indicating a narrowing of the vessel of interest at least one candidate position from the plurality of intravascular positions, wherein the at least one candidate position of the narrowing is identified as the first intravascular measurement position and a further intravascular position other than the at least one candidate position is identified as the second intravascular measurement position.

In some embodiments, the identifying of the first and second measurement positions may be performed using at least one diagnostic image of the vasculature including the vessel of interest that has been obtained by a respective imaging modality such as X-ray scanning, computed tomography (CT), X-ray angiography, positron emission tomography (PET), single photon emission computed tomography (SPECT), ultrasound imaging, or the like. In some specific embodiments, the at least one diagnostic image may particularly refer to a single two-dimensional X-ray angiography image.

In accordance with these embodiments, the first and second measurement positions are first identified by considering the at least one diagnostic image. Subsequently, a measurement of the hemodynamic value, such as the pressure value, is performed at the thus identified first and second measurement position.

For this purpose, the vessel of interest as imaged in the at least one diagnostic image is segmented into a plurality of segments. It shall be understood that the segmenting the vessel of interest corresponds to a segmenting of the vessel of interest as represented in the diagnostic image into respective vessel segments.

For each of the segments, a plurality of geometric parameter values for the vessel of interest may be derived at a plurality of intravascular positions. In this context, the term geometric parameter may refer to any parameter that is representative of the geometry of the vessel of interest. In some embodiments, the geometric parameter may particularly refer to the cross sectional area of the vessel of interest. In some embodiments, the geometric parameter may also refer to the inner shape of the vessel or similar geometric measures. Hereby, a value for at least one geometric parameter, such as a value for the cross sectional area, may be determined for a plurality of intravascular positions along the longitudinal axis of the vessel of interest. Accordingly, the plurality of geometric parameter values refers to the values determined respectively for each intravascular position along the longitudinal axis of the vessel of interest.

In some embodiments, the geometric parameter values are used to identify a lesion and/or a narrowing of the vessel of interest at least one intravascular position. The intravascular position at which the lesion and/or narrowing has been identified is then designated a candidate position, i.e. a potential candidate for the first measurement position. In case the lesion and/or narrowing has been identified at multiple intravascular positions, one of these intravascular positions may be selected as the candidate position. More specifically, the plurality of values for the geometric parameter indicating the geometry of the vessel are regarded and a change in the values is determined, which is indicative of a lesion and/or a narrowing in the vessel of interest. In one specific embodiment, the cross sectional area is considered as the geometric parameter and a change in said cross sectional area is regarded as indicating the lesion and/or the narrowing.

As previously mentioned, at such a position of a changed cross sectional area, the local flow velocity is significantly changed if a constant volumetric flow rate is assumed. Accordingly, the intravascular position of the lesion and/or narrowing as identified from the at least one diagnostic image may be considered a possible candidate for the first measurement position. Subsequently, an additional intravascular position located proximal or distal to the thus identified candidate position may be considered and designated as second measurement position. In the next step, the deriving of the first and second hemodynamic value of the first hemodynamic property is performed by measuring, at the first and second measurement position, the respective first hemodynamic property and acquiring the respective first and second value.

In some embodiments, the apparatus may further comprise a modeling unit for generating, on the basis of the at least one diagnostic image, a physiological model of the vessel of interest, the physiological model comprising a fluid dynamics model, wherein the computing the at least one diagnostic parameter representative of the second hemodynamic property is performed on the basis of the fluid dynamics model.

In some embodiments, a physiological model comprising a fluid dynamics model is used for computing the diagnostic parameter. Hereby, the physiological model may be obtained from at least one diagnostic image of the vessel of interest. In some embodiments, the physiological model may particularly be obtained from a single diagnostic image of the vessel of interest. The diagnostic image may hereby be used by a modeling unit to generate the physiological model from said diagnostic image. The generating of the physiological model may particularly comprise a segmentation of the imaged vessel of interest. This segmentation may be performed by the modeling unit for the purpose of generating the physiological model. Alternatively, the vessel segmentation performed by the identification unit for identifying the first and second measurement position may be used.

Based on this segmentation, a physiological model may be generated representing one or more vessel segments of the vessel of interest. To that end, the physiological model may comprise a fluid dynamics model to simulate the fluid dynamics, in particular of the blood, through the respective segments of the vessel of interest. To that end, the fluid dynamics model may be generated by performing calculations that simulate the interaction of the blood with the vessel wall, i.e. the inner surface of the vessel through which the blood is flowing. These interactions may be defined by respective boundary conditions that take account of certain hemodynamic properties of the vessel, such as vessel wall composition, vessel wall elasticity and vessel impedance, bifurcations in the vessel as well as blood viscosity. For this purpose, generalized boundary conditions may be used which are similar for all patients or for particular patient groups (distinguished by age, gender, physiological condition or the like). Alternatively or additionally, patient-specific boundary conditions that have been derived for a particular patient may be used for calculation of the fluid dynamics model.

In an embodiment, the fluid dynamics model may particularly refer to a lumped parameter model. In such a lumped parameter model, the fluid dynamics of the vessels are approximated by a topology of discrete entities. More particularly, in the lumped parameter model the vessel resistance is approximated by a series of resistor elements while the termination of a vessel is represented by an element representing ground. Thus, a vessel tree may be represented by a topology of resistors each having a particular resistance with the representation of the vessel tree being terminated by respective ground elements. These lumped parameter models reduce the number of dimensions compared to other approaches such as Navier-Stokes or the like. Accordingly, using a lumped parameter model may allow for a simplified calculation of the fluid dynamics inside the vessels and may ultimately result in reduced processing time.

Additionally or alternatively to the fluid dynamics model, the physiological model may also comprise a geometric model representing the geometric of the vessel of interest. The geometric model may hereby be a two-dimensional (2D) or three-dimensional (3D) geometric representation of the vessel of interest or a segment thereof. In a particular embodiment of the invention, the geometric model may be a 2D model derived from 2D angiographic image data for which a third dimension is approximated by assuming a circular shape of the vessel.

In some embodiments, the geometry and the fluid dynamics through each vessel (segment) may be simulated using the geometric model and the fluid dynamics model comprised in the physiological model, respectively. Accordingly, the computing of the diagnostic parameter representative of the second hemodynamic property may be performed using the fluid dynamics model by simulating a second hemodynamic parameter in the vessel of interest on the basis of respective boundary conditions as derived e.g. from the diagnostic data and/or the first and second hemodynamic value.

In some embodiments, the identifying of the first intravascular measurement position and the second intravascular measurement position further comprises determining, on the basis of the diagnostic image, a location of a bifurcation in the vessel of interest, and excluding the further intravascular position when it is determined that the bifurcation is located at a location proximate the further intravascular position along the longitudinal axis of the vessel of interest.

The above approach for computing the diagnostic parameter uses the approximation that no outflow of the blood from the vessel of interest occurs in the segment comprising the first and the second measurement position. In reality, the lesion and/or narrowing may be located in the proximity of bifurcations, i.e. a bifurcation may be identified proximal and/or distal to the lesion and/or narrowing. Through such a bifurcation part of the blood may outflow to (and inflow from) minor vessels, thereby resulting in a non-constant volumetric flow rate between the first measurement position and one or more intravascular positions that could be selected as the second measurement positions.

In this case, the selection has to include an exclusion of such intravascular positions in order to still obtain an accurate approximation of the second hemodynamic property. In other words: the first and second measurement position should be selected such that no outflow to minor vessels occurs between the first and the second measurement position. In that context, it shall be understood that the requirement that no outflow occurs shall be understood to also encompass the situation where the minor vessel (and the corresponding bifurcation) is small enough such that the outflow is neglectable from an accuracy point of view. Further, the term proximate may particularly refer to the bifurcation being located at a position in between the candidate position selected as first measurement position and the further intravascular position regarded as a potential second measurement position.

In order to achieve this objective, in some embodiments the at least one diagnostic image is used to identify vessel bifurcations along the vessel or vessel segment that is regarded for the assessment. The bifurcation may particularly be identified by deriving the bifurcation from the diagnostic image directly, either manually or by image processing, in case the bifurcation is directly visible in the diagnostic image.

Alternatively or additionally, the bifurcation may also be identified on the basis of one or more geometric parameters that have been determined from the diagnostic image for each segment of the vessel of interest as described herein above. This identification may particularly be performed by regarding the geometric parameter values for a plurality of intravascular positions in each vessel (segment) to detect localized changes (i.e. increases or decreases) in said geometric parameter value, which may be considered indications for vessel bifurcations. In some embodiments, this geometric parameter value may particularly be derived using an estimation based on the geometric model included in the physiological model.

Hence, once the bifurcation has been identified in between the candidate position designated as first measurement position and at least one further intravascular position other than the candidate position, said at least one intravascular position may be excluded as a potential second measurement position. That is, the particular intravascular position is found to be unsuitable as second measurement position due to the bifurcation being proximate to the intravascular position and a different second measurement position may be identified. In case no suitable second measurement position may be found, the apparatus may then attempt to identify a different first measurement position. Alternatively or additionally, an outflow correction may be performed, correcting the approximation for the outflow through the bifurcation.

Accordingly, in some embodiments, the identifying of the first intravascular measurement position and the second intravascular measurement position further comprises a determining, on the basis of the diagnostic image, a location of a bifurcation in the vessel of interest proximate to the further intravascular position and the computing the at least one diagnostic parameter on the basis of the fluid dynamics model comprises a correcting of the at least one diagnostic parameter by simulating an outflow through said bifurcation using the fluid dynamics model.

In some embodiments, no exclusion of the second measurement position is performed in case of a bifurcation being present in between the first and the second measurement position. Rather, an approach is followed in which the computation of the second hemodynamic property is corrected such as to account for the outflow through the bifurcation.

As indicated herein above, in case of vessel bifurcations in between the first and the second measurement position, the volumetric flow rate Q is not constant for both positions. Rather, the volumetric flow rate $Q_2$ at the second measurement position differs from the volumetric flow rate $Q_1$ at the first measurement position by the local outflow rate $\Delta Q$:

$$Q_2 = Q_1 - \Delta Q.$$

The local outflow rate $\Delta Q$ may particularly be modeled using the fluid dynamics model comprised in the physiological model. More specifically, the size and position of the bifurcation may be used as additional boundary conditions in the fluid dynamics model to simulate the outflow rate from the respective bifurcation.

In some embodiments, Murray's law may be used to determine the outflow through a respective bifurcation. According to Murray's law the following relation holds:

$$Q = k*D^3.$$

Hereby, Q corresponds to the volumetric flow rate, D is the vessel diameter and k is a proportionality constant. It shall be understood that, although in the exemplary embodiment, Murray's law is used to determine the volumetric flow rate Q, other correlations Q(D) may also be used to describe the relation between volumetric flow rate and vessel diameter, in particular for other parts of the vasculature.

As previously indicated, the outflow rate may be represented by the difference between the volumetric flow rate at the first measurement position and the volumetric flow rate at the second measurement position, in between which the bifurcation is located $$\Delta Q = Q_1 - Q_2,$$

The physiological model comprising the fluid dynamics model may thus model the local outflow rate using Murray's law by estimating the proportionality constant in the vessel and modeling the vessel diameter $D_1$, $D_2$ at the first and second measurement position on the basis of the diagnostic image data. This allows to determine the volumetric flow rate at the first and second measurement position using Murray's law:

$$Q_1 = k*D_1^3, Q_2 = k*D_2^3.$$

The local outflow rate $\Delta Q$ may be simulated as the difference between the thus determined values $Q_1$, $Q_2$.

In some embodiments, where the fluid dynamics model may be a lumped parameter model and the outflow through the bifurcation may be estimated by means of a respective resistor element which outlet resistance is dependent on the size of the bifurcation as derived from the diagnostic image.

In some further embodiments, the computing the at least one diagnostic parameter on the basis of the fluid dynamics model comprises a correcting of the at least one diagnostic parameter by simulating a vessel friction between the first intravascular measurement position and the second intravascular measurement position using the fluid dynamics model.

In some embodiments, the pressure loss between the first and the second measurement location due to friction may be considered in the computation of the second hemodynamic property. This may particularly be performed in case the pressure losses due to friction are too significant to be neglected in an accurate approximation of the diagnostic parameter representative of the second hemodynamic property. In this case, the relation between the pressure values at the first and second measurement position becomes $$p_1 - p_2 - \Delta p_F = \frac{\rho}{2}(v_2^2 - v_1^2),$$

where $\Delta p_F$ corresponds to the pressure loss due to friction.

Hereby, the pressure loss $\Delta p_F$ has to be estimated. This may particularly be performed by including a respective boundary condition into the fluid dynamics model which simulates the pressure loss along the vessel of interest, including the pressure loss in between the first and second measurement position. In some embodiments, where the fluid dynamics model is implemented as a lumped parameter model, the friction may be simulated by means of a respective resistor element. In some embodiments, a finite element approach may alternatively be used.

In some embodiments, the diagnostic data comprises intravascular pullback data comprising a plurality of hemodynamic values of the first hemodynamic parameter acquired in-situ by means of a pullback recording at a plurality of intravascular positions along a longitudinal axis of the vessel of interest. Further, the identifying of the first intravascular measurement position and the second intravascular measurement position comprises identifying, from the plurality of hemodynamic values acquired at the plurality of intravascular positions, at least one hemodynamic value exhibiting a localized change at least one candidate position from the plurality of intravascular positions, wherein the at least one candidate position is identified as the first intravascular measurement position and a further intravascular position other than the at least one candidate position is identified as the second intravascular measurement position.

In some embodiments, the diagnostic data may comprise pullback data that has been obtained in-situ from the vessel of interest. In some embodiments, the pullback data may particularly refer to pressure pullback data. As previously indicated, pullback data is acquired by pulling a measurement wire through a vessel of interest for a particular pullback length and acquiring a plurality of measurement values for a plurality of intravascular positions along said pullback length. In case of pressure pullback data being acquired, the measurement device used may typically be a wire comprising a pressure probe. The pressure probe is then used to collect a plurality of pressure values at a plurality of intravascular positions, thereby resulting in a respective pressure pullback curve, i.e. curve representing the pressure values as a function of the intravascular position.

A thus obtained pressure curve may exhibit a localized change, i.e. a localized increase or decrease in the pressure value at one or more particular intravascular positions. As previously indicated herein above, according to Bernoulli's law, a change in pressure (value) also indicates a change in flow velocity. More specifically, a decrease in the pressure value causes an increase in flow velocity and vice versa. Accordingly, a localized change in the pressure value indicates a suitable candidate position for the first measurement position. Hence, each of the intravascular positions at which a localized change is detected may be used as the candidate position for the first measurement position. Subsequently, a further intravascular measurement position proximal or distal to the candidate position (i.e. the first measurement position) is identified as the second measurement position.

Using pressure pullback data to identify the first and second measurement position avoids the necessity of performing two measurements, one for identifying the measurement positions and one for deriving the first and second hemodynamic value. Rather, in this approach, the deriving of the first and second hemodynamic value may be directly performed on the already acquired pullback curve, by selecting the respective values of said curve for the first and second measurement position.

It shall be understood that this approach does not allow to derive the cross sectional area of the vessel. Accordingly, the volumetric flow rate may not be determined from the pullback data alone. However, since the Coronary Flow Reserve (CFR) as a clinically relevant index, may be approximated without knowledge of the volumetric flow rate according to $$CFR = \sqrt{\frac{\Delta p_H}{\Delta p_R}},$$

the CFR as a diagnostic parameter indicative of the flow may still be directly obtained from the pressure pullback data. Hence, this embodiment may represent a straightforward approach for determining clinically relevant diagnostic parameters which do not require knowledge of the vessel geometry to be determined.

In one or more further embodiments, the diagnostic data further comprises at least one diagnostic image of the vessel of interest. Further, the identifying of the first intravascular measurement position and the second intravascular measurement position comprises co-registering of the at least one diagnostic image to the intravascular pressure data, and indicating the first intravascular measurement position and the second intravascular measurement position in the at least one diagnostic image.

In some embodiments, the pressure pullback data may further be used to obtain a diagnostic parameter that requires the determination of a geometric parameter, such as the cross sectional area. For this purpose, the diagnostic data may further comprise at least one diagnostic image. The diagnostic image and the pullback data may be co-registered. Co-registering the diagnostic image and the pullback data refers to a process in which, for each or some of the intravascular positions of the pullback data, a corresponding vessel position in the diagnostic image of the vessel of interest is determined. Accordingly, the two measurement modalities are put in relation to one another.

Such a co-registration allows to determine the vessel positions in the diagnostic image that correspond to the first and second measurement position identified from the pullback data. These vessel positions may then be indicated in the diagnostic image.

To that end, the term indicating may particularly refer to a process internal the apparatus, in which the apparatus in provided with the information of which position in the imaged vessel corresponds to the first and second measurement position. On the basis of this indication, the apparatus may then perform a plurality of image processing steps or the like, to obtain information about the vessel geometry, and, accordingly, about the volumetric flow. In some embodiments, the apparatus may particularly derive the cross sectional area at the first and second measurement position from the diagnostic image. To that end, the apparatus may employ the modeling unit to generate a physiological model for a vessel segment encompassing the first and second measurement position. This physiological model may comprise a fluid dynamics model and/or a geometric model. The apparatus may use the geometric model to derive the geometric parameter values, e.g. the cross sectional area, at least at the first and second measurement position.

Further, the apparatus may use the indication to generate a graphical representation of the imaged vessel including a first and/or a second indicator, such as an arrow or a circle, highlighting the first and second measurement position in the diagnostic image. The apparatus may then cause a display unit to display such graphical representation. This may allow a user, in particular a physician, to visually confirm a suitable selection of the first and second measurement position.

In this context, it shall be understood that the case where the diagnostic image is used to generate a graphical representation of the vessel of interest is not limited to the case where the diagnostic data comprises pullback data. Likewise, it is possible for the apparatus to generate a graphical representation of the imaged vessel in case the diagnostic data comprises image data. In this case, upon identification of the first and second measurement position, the apparatus may directly use this identification to insert the respective indicators into the graphical representation and provide the thus generated graphical representation to a respective display unit. This display unit may particularly comprise a computer screen, an LCD display or the like.

In some embodiments, the computing the at least one diagnostic parameter comprises a determining of a coronary flow reserve and/or a volumetric flow rate and/or flow velocity of the blood flow in the vessel of interest.

The first and second hemodynamic value obtained at the first and second measurement position may particularly be used to compute a diagnostic parameter representative of the Coronary Flow Reserve (CFR), the volumetric flow rate Q, the flow velocity v or like hemodynamic properties. In this context, the computing may be performed particularly well in case the first hemodynamic property measured at the first and second measurement position relates to the pressure inside the vessel of interest. As elaborated herein above, the pressure values allow for a computation of the flow-related properties according to respective fluid dynamics laws, such as Bernoulli's law, Murray's law and so on.

According to a further aspect, a method for assessing a coronary vasculature is provided. The method comprises the steps of receiving diagnostic data of a vessel of interest in the vasculature for identifying, using the diagnostic data, a first intravascular measurement position, wherein a first hemodynamic value of a first hemodynamic property is derived at said first intravascular measurement position and a second intravascular measurement position, wherein a second hemodynamic value of the first hemodynamic property is derived at said intravascular second measurement position, and computing, on the basis of the first hemodynamic value and the second hemodynamic value, at least one diagnostic parameter representative of a second hemodynamic property in the vessel of interest.

In some embodiments, the method may further comprises that the identifying the first measurement position and the second measurement position comprises indicating, to a user, a first and second measurement position.

In some embodiments, the method further comprises a step in which the user is presented with the identified first and second measurement positions by means of a respective indication. This indication may particularly relate to a visual indication, by means of a graphical representation of the vessel of interest and respective indicators to the first and second measurement position. Alternatively or additionally, the indication may also be audible or visual in the sense that the position relative to the longitudinal axis of the vessel interest is indicated in spoken or written form.

In response to the indication, the user may then position the intravascular measurement device accordingly, in order to obtain the first hemodynamic value at the first measurement position and the second hemodynamic value at the second measurement position. That is, the user introduces the intravascular measurement device into the vessel of interest and adjusts the position such that the measurement probe, such as the pressure probe in case of a pressure measurement, is located at the first measurement position and, subsequently, at the second measurement position. It shall be understood that the intravascular measurement device may likewise first be positioned at the second measurement position and subsequently be moved to the first measurement position.

The indicating to the user may further comprise other indications. In some embodiments, these indications may particularly relate to further information of the vessel of interest and/or the procedure performed in order to assess it. To that end, the indicating may comprise providing information about the diagnostic measurement modality used to obtain the diagnostic data, providing information about the patient's health status and/or co-morbidities or the like. In some embodiments, the indicating may particularly comprise an indicating that no first and/or second measurement position could be identified for a particular vessel (segment) of interest.

In a further aspect, a computer program for controlling an apparatus according to any of the above embodiments is provided, which, when executed by a processing unit, is adapted to perform the method according to one or more of its embodiments. In an even further aspect, a computer-readable medium having stored there on the computer program is provided.

It shall be understood that the apparatus of claim 1, the method of claim 12, the computer program according to 14, and the computer readable medium of claim 15, have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
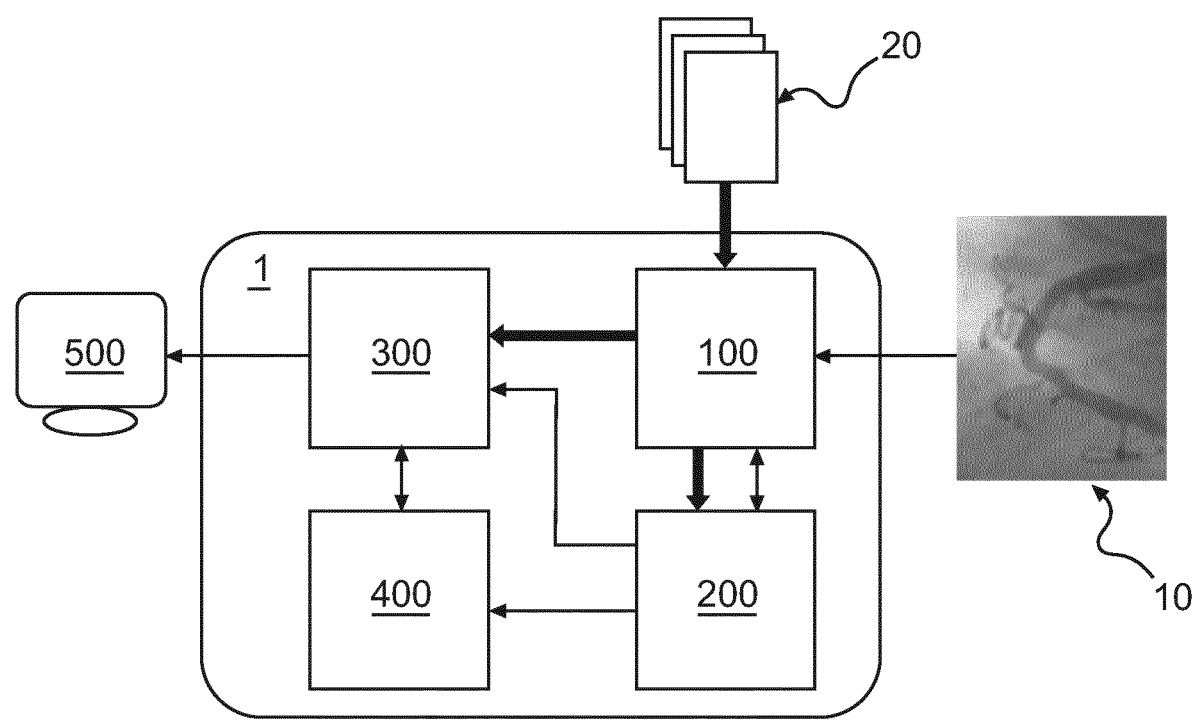
FIG. 1 schematically illustrates an apparatus for assessing a coronary vasculature according to a first exemplary embodiment.

The illustration in the drawings is schematically. In different drawings, similar or identical elements are provided with the same reference numerals.

FIG. 1 represents schematically an exemplary embodiment of an apparatus 1 for assessing a hemodynamic property. The apparatus 1 comprises an input unit 100, an identification unit 200, a computation unit 300, a modeling unit 400 and a display unit 500.

The input unit 100 receives a diagnostic image 10 of a vessel of interest. In the exemplary embodiment according to FIG. 1, diagnostic image 10 is a two-dimensional image acquired using X-ray angiography. The input unit 100 provides the diagnostic image 10 to the identification unit 200.

The identification unit 200 is configured to receive the diagnostic image 10 and to perform a vessel segmentation of the vessel of interest represented in the diagnostic image 10, i.e. the identification unit 200 segments the (image of the) vessel of interest in a plurality of segments along a longitudinal axis of the vessel of interest. The identification unit 200 considers the segments and derives, for each intravascular position in each vessel segment, a value of one or more geometric parameters. In the exemplary embodiment according to FIG. 1, one geometric parameter derived by the identification unit 200 is the cross sectional area of the vessel. The identification unit 200 thus derives for each intravascular position in a respective vessel segment, a corresponding cross sectional area of the vessel.

Based on the cross sectional area, the identification unit 200 may then determine an intravascular position at which a change in cross sectional area is observed. In the exemplary embodiment according to FIG. 1, identification unit particularly determines an intravascular position at which a narrowing of the vessel is located. For this purpose, the identification unit 200 may compare the cross sectional area determined for each intravascular position in each segment and determine where the cross sectional area at one particular intravascular position in one particular segment is smaller compared to the remaining intravascular positions. The intravascular position exhibiting a smaller cross section is then designated as a candidate for the first measurement position. Subsequently, the candidate position is designated the first measurement position.

The identification unit 200 then regards a further intravascular position other than the candidate position designated as the first measurement position and identifies this further intravascular position as the second measurement position. In the exemplary embodiment according to FIG. 1, the further intravascular position corresponds to a position located about 1 cm distal from the candidate position when viewing along the longitudinal axis of the vessel of interest. The identification unit 200 then provides the information about the first and second measurement position to the input unit 100.

In response to receiving the information about the first and second measurement position identified by the identification unit 200, the input unit 100 is configured to receive hemodynamic measurement data 20 representative of a first hemodynamic property. The hemodynamic measurement data 20 thus comprises a first hemodynamic value of the first hemodynamic property measured at the first measurement position and a second hemodynamic value of the first hemodynamic property measured at the second measurement position.

The input unit 100 may particularly receive the hemodynamic measurement data 20 comprising the first and second hemodynamic value by providing an instruction to the intravascular measurement device installed for acquiring hemodynamic measurement data by means of an in-situ measurement to acquire the first and second hemodynamic value at the first and second measurement position or by indicating, e.g. via a graphical user interface, a user the first and second measurement position such that the user may perform respective measurements at the first and second measurement position indicated.

In the exemplary embodiment according to FIG. 1, the hemodynamic measurement data 20 corresponds to a pressure measurement acquired while the patient was at rest. Accordingly, the first and second hemodynamic value acquired at the first and second measurement position correspond to a first pressure value $p_1$ and second pressure value $p_2$.

When the first pressure value $p_1$ and the second pressure value $p_2$ are received by the input unit 100, the input unit 100 is configured to provide the pressure values $p_1$, $p_2$ to computation unit 300. The computation unit 300 is configured to calculate, from the pressure values, at least one diagnostic parameter indicative of a hemodynamic property of the vessel of interest.

In the exemplary embodiment according to FIG. 1, the computation unit 300 particularly computes the volumetric flow rate through the respective segment of the vessel of interest and outputs the information about the computed volumetric flow rate along with the information about the measurement positions, and, optionally with further information about the pressure values used for computation, to the modeling unit 400.

Further, the modeling unit 400 is configured to receive, from the identification unit 200, an indication that a bifurcation is present between the first and second measurement position as indicated by the input unit 100. To that end, identification unit 200 is particularly configured to detect, based on the diagnostic image 10, the presence of such a bifurcation by a respective image processing algorithm. In some embodiments, the detection may also be performed on the basis of at least one geometric parameter value derived for the vessel (segment).

The modeling unit 400 receives the computed volumetric flow rate from computation unit 300. This approximated volumetric flow rate does not yet regard the bifurcation that is present between the two measurement positions. Accordingly, the approximated flow rate does not account for the outflow rate from the vessel of interest in between the measurement positions.

The modeling unit 400 further receives the diagnostic image 10 and/or the segmentation of the vessel of interest via identification unit 200. Further, modeling unit 400 receives the information about the identified bifurcation.

Depending on the received information, modeling unit 400 then either segments the vessel of interest in the diagnostic image or uses the vessel segmentation received from the identification unit 200 to generate a physiological model of the vessel of interest comprising a fluid dynamics model representative of the fluid dynamics through the vessel of interest (or a segment thereof). Optionally, the modeling unit 400 further includes a geometric model of the geometry of the vessel of interest into the physiological model.

Using the fluid dynamics model comprised in the physiological model, the modeling unit 400 models the outflow through the bifurcation indicated by the identification unit 200 as well as the pressure loss due to friction in between the first and second measurement position and corrects the computed volumetric blood flow accordingly.

The modeling unit 400 then provides the corrected volumetric flow rate to computation unit 300 which may uses the corrected volumetric flow rate to compute at least one diagnostic parameter representative thereof. To that end, the diagnostic parameter may particularly correspond to the value of the volumetric metric flow rate at a particular position inside the vessel. Alternatively, the computed diagnostic parameter may relate to an index derived from the volumetric flow rate.

The computation unit 300 then provides the diagnostic parameter, optionally along with the diagnostic image 10 to the display unit 500. Display unit 500 generates, on the basis of the information provided by the computation unit 300, a graphical representation of the at least one diagnostic parameter. Optionally, the display unit 500 may further generate a graphical representation of the diagnostic image and display said graphical representation along with the graphical representation of the diagnostic parameter. In some embodiments, the diagnostic parameter may particularly be displayed as part of the graphical representation of the image, particularly placed at the position in the image which corresponds to the intravascular position for which the diagnostic parameter was derived. The graphical representation may then be provided to a user for further information, e.g. about the hemodynamic values for the first hemodynamic property and/or the diagnostic parameter indicative of the second hemodynamic property.

Figure 2:
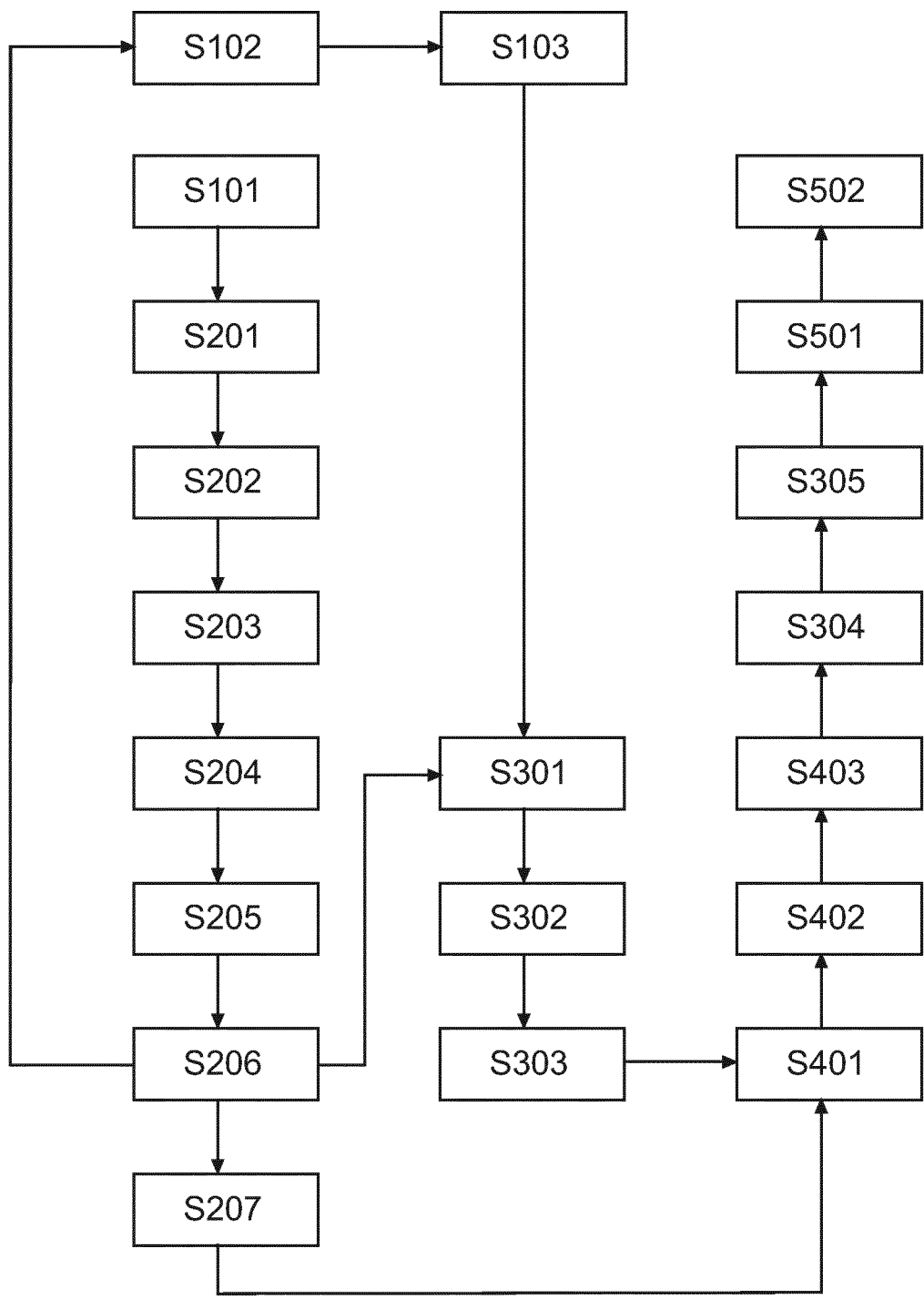
FIG. 2 represents a flow chart for a method for assessing a coronary vasculature according to the first exemplary embodiment, FIG. 3 schematically illustrates an apparatus for assessing a coronary vasculature according to a second exemplary embodiment.

FIG. 2 illustrates a flow chart representing a method to be performed by the apparatus according to the first embodiment of FIG. 1.

In step S101, the input unit 100 receives a diagnostic image 10 of a vessel of interest and provides the diagnostic image 10 to identification unit 200.

In step S201, identification unit 200 receives the diagnostic image 10 and performs, in step S202, a vessel segmentation of the vessel of interest represented in the diagnostic image 10. In step S203, the identification unit 200 derives, for each intravascular position in each vessel segment, a value of one or more geometric parameters, which corresponds, in this particular embodiment, to the cross sectional area of the vessel.

In step S204, the identification unit 200 compares the cross sectional area determined for each intravascular position in each segment to one another and determines an intravascular position at which the cross sectional area is significantly different from the remaining cross sectional areas at the remaining intravascular positions. In the exemplary embodiment of FIG. 2, the identification unit particularly determines at least one intravascular position at which the cross sectional are shows a localized decrease.

In step S205, the intravascular position at which the localized decrease in cross sectional area was determined is designated as the first measurement position. Further, a further intravascular position other than the first measurement position is identified as the second measurement position. The identification unit 200 then provides the information about the first and second measurement position to the input unit 100 and the geometric parameters derived at the first and second measurement position to computation unit 300 in step S206.

Further, in step S207, the identification unit 200 determines whether bifurcations are present between the first and second measurement position and provides this information, along with the diagnostic image and, optionally, the segmentation, to modeling unit 400.

In step S102, the input unit 100 receives, in response to receiving the information about the first and second measurement position, hemodynamic measurement data 20 comprising a first hemodynamic value of a first hemodynamic property measured at the first measurement position and a second hemodynamic value of the first hemodynamic property measured at the second measurement position. In the exemplary embodiment according to FIG. 2, the first and second hemodynamic values particularly correspond to a first pressure value $p_1$ and second pressure value $p_2$. In step S103, the input unit 100 provides the pressure values $p_1$, $p_2$ to computation unit 300.

In step S301, the computation unit 300 receives the pressure values from input unit 100 and the geometric parameter values from identification unit 200. In step S302, the computation unit 300 uses the pressure values, optionally along with the geometric parameter values, to compute at least one diagnostic parameter indicative of a hemodynamic property of the vessel of interest. In the exemplary embodiment according to FIG. 2, the computation unit 300 particularly computes the volumetric flow rate through the respective segment of the vessel of interest and outputs the information about the computed volumetric flow rate along with the information about the measurement positions, and, optionally with further information about the pressure values used for computation, to the modeling unit 400 in step S303.

In step S401, the modeling unit 400 receives an indication that a bifurcation is present between the first and second measurement position along with diagnostic image 10 and/or the segmentation of the vessel of interest from the identification unit 200. Also in step S401, the modeling unit 400 receives the computed volumetric flow rate, along with the information about the measurement positions and, optionally, with further information about the pressure values used for computation, from computation unit 300.

In step S402, modeling unit 400 either segments the vessel of interest in the diagnostic image or uses the vessel segmentation received from the identification unit 200 to generate a physiological model of the vessel of interest comprising a fluid dynamics model representative of the fluid dynamics through the vessel of interest, optionally including a geometric model of the vessel of interest into the physiological model.

On the basis of the fluid dynamics model, the modeling unit 400 models, in step S403, the outflow through the bifurcation as well as the pressure loss due to friction in between the first and second measurement position and corrects the computed volumetric blood flow accordingly. In step S404, the modeling unit 400 provides the corrected volumetric flow rate to computation unit 300.

In step S304, the computation unit 300 uses the received corrected volumetric flow rate to compute at least one diagnostic parameter representative thereof and provides said diagnostic parameter, optionally along with the diagnostic image 10, to the display unit 500 in step S305.

In step S501, display unit 500 receives the diagnostic parameter and the at least one diagnostic image and generates, on the basis thereof, a graphical representation of the at least one diagnostic parameter and, optionally, of the diagnostic image. In step S502, display unit then displays the graphical representation to a user.

Figure 3:
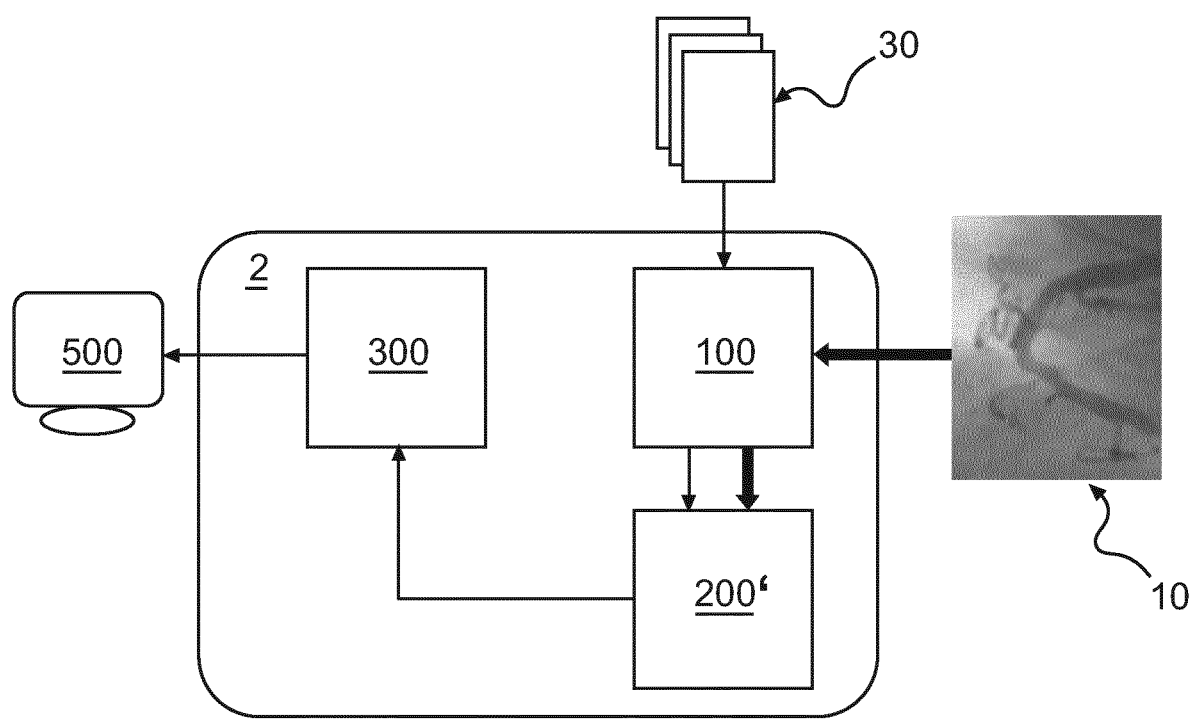

FIG. 3 schematically illustrates an apparatus 2 for assessing a coronary vasculature according to a second exemplary embodiment. The apparatus 2 comprises an input unit 100, an identification unit 200', a computation unit 300 and a display unit 500. The input unit 100 is configured to receive diagnostic data comprising intravascular pullback data 30. In the particular embodiment of FIG. 3, the intravascular pullback data 30 corresponds to pressure pullback data comprising a plurality of pressure values obtained at a plurality of intravascular positions along a longitudinal axis of the vessel of interest. Further, the input unit 100 receives at least one diagnostic image 10.

The input unit 100 provides the pressure pullback data to the identification unit 200'. The identification unit 200' regards the pressure pullback curve, i.e. a curve representing the plurality of pressure values as a function of the intravascular position and determines a localized change in the pressure value. More particularly, in the exemplary embodiment according to FIG. 3, the identification unit 200' determines the intravascular position at which a local minimum occurs in the pullback curve. The intravascular position corresponding to the local minimum in the pullback curve is considered a candidate for the first measurement position. To that end, the identification unit 200' is particularly configured to derive one or more intravascular positions, each corresponding to a local minimum of the pullback curve, as candidate positions and to, subsequently, identify one of the candidate positions as the first measurement position. Subsequently, the identification unit 200' determines a further intravascular position other than the candidate position selected as the first measurement position as the second measurement position.

The identification unit 200' then co-registers the pullback data with the diagnostic image 10 received from the input unit 100. Accordingly, the identification unit 200' determines which intravascular position in the pressure pullback data corresponds to which position in the vessel of interest as represented by the diagnostic image. Based on the co-registration, the identification unit 200' may particularly determine whether there are any bifurcations present between the first and the second measurement position and may, in case it is determined that a bifurcation is present, either disregard the selected second measurement position and select a new one or disregard the selected first and second measurement position and select, from the plurality of candidate positions, a new first measurement position and a corresponding new second measurement position. Alternatively, the identification unit 200' may also decide to ignore the bifurcation, in particular, if the identification unit determines that the bifurcation is to a very minor vessel the outflow rate to which is neglectable. In that context, it shall be understood that the co-registration and subsequent bifurcation identification may also be performed prior to selecting the first measurement position from the plurality of candidate positions.

Since the pressure values have already been collected during the pullback recording of the pullback data, the identification unit 200' may then directly determine the first and second hemodynamic values, i.e. the first and second pressure values, at the first and second measurement position from the pressure pullback curve.

The identification unit 200' then provides the determined pressure values $p_1$, $p_2$, optionally along with the co-registered diagnostic image and possible further information about bifurcations or the like, to the computation unit 300.

The computation unit 300 may use the pressure values $p_1$, $p_2$ received from the input unit to determine a diagnostic parameter. Since the computation unit 300 in this embodiment has no knowledge about any geometric parameters related to the vessel of interest, the computation is limited to diagnostic parameters which do not require such knowledge. In the particular embodiment according to FIG. 3, the pressure values $p_1$, $p_2$ are used to compute the Coronary Flow Reserve (CFR). In order to do so, the pressure values have to be derived from two sets of pressure pullback data, one recorded in a resting state and one under hyperemia.

The computation unit 300 then provides the computed diagnostic parameter, optionally along with the diagnostic image 10 and first and second measurement position co-registered thereto, to the display unit 500. The display unit 500 then generates a graphical representation of the diagnostic parameter and, optionally, of the diagnostic image 10. In the exemplary embodiment according to FIG. 3, the graphical representation generated by the display unit 500 corresponds to a graphical representation of the diagnostic image 10, in which the first and second measurement position are visually indicated and the calculated diagnostic parameter is represented.

Figure 4:
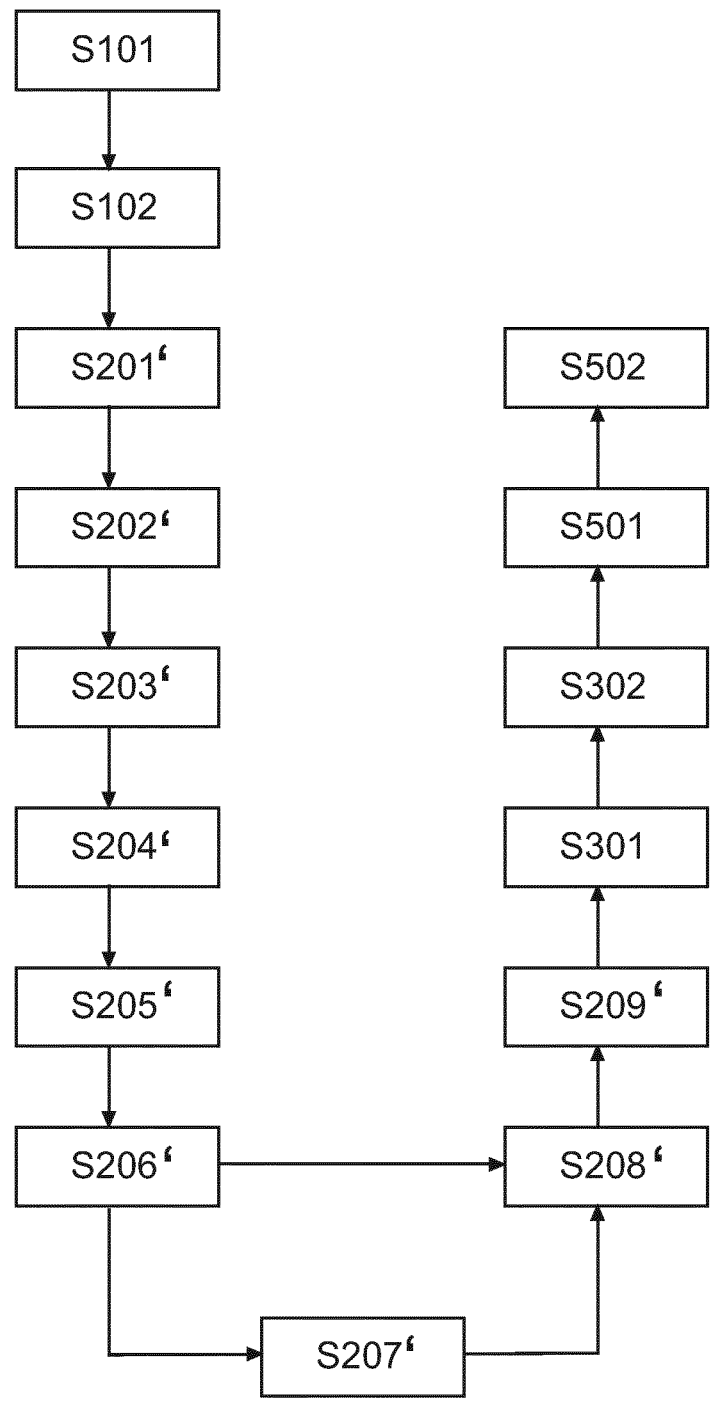
FIG. 4 represents a flow chart for a method for assessing a coronary vasculature according to the second exemplary embodiment.

FIG. 4 represents a flow chart for a method for assessing a coronary vasculature according to the second exemplary embodiment.

In step S101, the input unit 100 receives diagnostic data comprising intravascular pullback data 30. More specifically, in the exemplary embodiment according to FIG. 4, the input unit 100 receives pressure pullback data comprising a plurality of pressure values obtained at a plurality of intravascular positions. Further, the input unit 100 receives at least one diagnostic image 10 in step S101. In step S102, the input unit 100 provides the pressure pullback data to the identification unit 200'.

In step S201', the pressure pullback data 30 is received at the identification unit 200'. The identification unit 200' derives, from the pressure pullback data, a respective pressure pullback curve in step S202' and determines, using the pressure pullback curve, localized changes in the pressure values obtained during the pullback recording at the plurality of intravascular positions. In the exemplary embodiment according to FIG. 4, the identification unit 200' particularly identifies local minima and/or maxima in the pullback curve. In step S203', the identification unit 200' designates the intravascular positions corresponding to the local minima and maxima as potential candidate positions and selects, in step S204', one particular candidate position as the first measurement position and a further intravascular position, typically located distal or proximal to the candidate position, as the second measurement position.

In step S205', identification unit 200' co-registers the diagnostic image 10 to the pressure pullback data 30 and, in step S206', uses the co-registration to determine whether bifurcations are present between the first and second measurement position.

If there is no bifurcation in between the first and second measurement position, identification unit directly proceeds to step S208', in which the identification unit derives, from the pressure pullback data, pressure values $p_1$, $p_2$. In case a bifurcation is detected, the identification unit 200' first reselects, in step S207', the first and/or second measurement position as described above or, alternatively, ignores the bifurcation. Only after reselection (or decision to ignore) the identification unit 200' proceeds to step S208'.

Once the pressure values $p_1$, $p_2$ have been obtained in step S208', identification unit 200 provides these pressure values $p_1$, $p_2$, optionally along with the co-registered diagnostic image and possible further information, to the computation unit 300 in step S209'.

In step S301, the computation unit 300 receives the pressure values $p_1$, $p_2$ and computes, in step S302, a diagnostic parameter on the basis of the pressure values. In the particular embodiment according to FIG. 4, the computation unit 300 particularly computes the CFR using the received pressure values $p_1$, $p_2$, which, as indicated above, the computation unit 300 has to receive for both, the resting state and the hyperemic state. are used to compute the Coronary Flow Reserve (CFR).

In step S302, the computation unit 300 then provides the computed diagnostic parameter, optionally along with the diagnostic image 10 and the information about the first and second measurement position that have been co-registered to the diagnostic image 10, to the display unit 500.

In step S501, the display unit 500 receives the diagnostic parameter, optionally along with the diagnostic image 10 and the further information. In step S502, the display unit generates a graphical representation of the diagnostic parameter and, optionally, of the diagnostic image 10 and presents the graphical representation to the user.

Although in above described embodiments, the diagnostic images have been obtained using X-ray angiography, it shall be understood that in other embodiments, the diagnostic images may be retrieved by other imaging methods, such as helical computed tomography or sequential computed tomography, magnetic resonance imaging, ultrasound imaging, or the like.

Further, it shall be understood that, although in the above embodiments, the identification unit and the modeling unit are implemented as two separate entities, the identification unit and the modeling unit may also correspond to the same entity. More specifically, they may be implemented as respective modules and/or a computer program to be executed by a processing device.

Further, while in the above embodiments, the assessment has been performed for the coronary physiology, in other embodiments, the modeling may likewise be performed on other physiologies of the human body. As an example, the approach may be applied to assess the peripheral arteries in the human body.

It may be further understood that while in the above-embodiments, the cross sectional area of the vessel and the respective vessel diameter have been used as geometric parameters, other geometric parameters may likewise be derived.

Although in the above described embodiments the diagnostic parameter indicative of the hemodynamic property is related to the volumetric blood flow and/or the coronary flow reserve, it is to be understood that, likewise, other diagnostic parameters may be derived, such as blood velocity, blood pressure, blood viscosity, vessel wall friction, or the like.

Further, it shall be understood that, also in the above described embodiments the fluid outflow from the vessel of interest through respective vessel branches has been assessed and modeled, the principles described above may likewise be used to assess and model the fluid inflow into the vessel of interest.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the receiving of diagnostic data, the identifying of the first and second measurement position, the generating of a physiological model, the computation of the diagnostic parameter et cetera performed by one or several units or devices can be performed by any other number of units or devices. These procedures in accordance with the invention can hereby be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to an apparatus for assessing a hemodynamic property in a coronary vasculature comprising an input unit for receiving diagnostic data of a vessel of interest in the vasculature and an identification unit for identifying, using the diagnostic data a first measurement position, wherein a first hemodynamic value of a first hemodynamic property is derived at said first measurement position, and a second measurement position, wherein a second hemodynamic value of the first hemodynamic property is derived at said second measurement position. The apparatus further comprises a computation unit for computing, on the basis of the first hemodynamic value and the second hemodynamic value, at least one diagnostic parameter representative of a second hemodynamic property in the vessel of interest.

By means of this apparatus suitable measurement positions for measuring a first hemodynamic property in-situ may be identified, thus allowing to approximate diagnostic parameters concerning a second hemodynamic property, different from the first hemodynamic property, without the necessity to directly measure said second hemodynamic property.

The invention claimed is:

1. An apparatus for assessing a coronary vasculature comprising:
   an input unit configured for receiving:
      intravascular pressure data of a vessel of interest in the vasculature of a patient obtained by an intravascular device at a plurality of measurement positions within the vessel of interest; and
      at least one diagnostic image;
   an identification unit configured for:
      identifying a first intravascular measurement position of the plurality of measurement positions;
      deriving a first intravascular pressure value using the intravascular pressure data obtained by the intravascular device at the first intravascular measurement position;
      identifying a second intravascular measurement position of the plurality of measurement positions;
      deriving a second intravascular pressure value using the intravascular pressure data obtained by the intravascular device at the second intravascular measurement position;
      registering the at least one diagnostic image and the intravascular pressure data; and
      determining, based on the registration, if a vessel feature affecting at least one of a flow velocity or a flow rate in the vessel of interest is positioned between the first intravascular measurement position and the second intravascular measurement position;
   a computation unit configured for computing, if no vessel feature is determined, at least one of the flow velocity or the flow rate in the vessel of interest based on the first intravascular pressure value at the first intravascular measurement position and the second intravascular pressure value at the second intravascular measurement position; and
   a display unit configured for displaying a graphical representation of the at least one of the flow velocity or the flow rate.

2. The apparatus according to claim 1, wherein identifying the first intravascular measurement position and identifying the second intravascular measurement position comprise:

predicting a localized change in the at least one of the flow velocity or the flow rate in the vessel of interest at one or more candidate position(s), identifying the one or more candidate position(s) as the first intravascular measurement position; and identifying an intravascular position other than the one or more candidate position(s) as the second intravascular measurement position.

3. The apparatus according to claim 1, wherein identifying the first intravascular measurement position and identifying the second intravascular measurement position comprise:

segmenting the vessel of interest into a plurality of segments;

deriving, for each of the segments, a plurality of geometric parameter values for the vessel of interest at a plurality of intravascular positions along a longitudinal axis of the vessel of interest;

identifying, from the plurality of geometric parameter values at the plurality of intravascular positions, at least one geometric parameter value indicating a narrowing of the vessel of interest at one or more candidate position(s) from the plurality of intravascular positions; wherein the one or more candidate position(s) of the narrowing is identified as the first intravascular measurement position and a further intravascular position other than the one or more candidate position(s) is identified as the second intravascular measurement position.

4. The apparatus according to claim 3, further comprising:

a modeling unit configured for generating, on the basis of the at least one diagnostic image, a physiological model of the vessel of interest, the physiological model comprising a fluid dynamics model;

wherein the computing the at least one of the flow velocity or the flow rate is performed on the basis of the fluid dynamics model.

5. The apparatus according to claim 3, wherein identifying the first intravascular measurement position and identifying the second intravascular measurement position further comprise:

determining, on the basis of the diagnostic image, a location of a bifurcation in the vessel of interest; and excluding the further intravascular position when it is determined that the bifurcation is located at a location proximate the further intravascular position along the longitudinal axis of the vessel of interest.

6. The apparatus according to claim 3, wherein identifying the first intravascular measurement position and identifying the second intravascular measurement position further comprise:

determining, on the basis of the diagnostic image, a location of a bifurcation in the vessel of interest proximate to the further intravascular position; and the computing the at least one of the flow velocity or the flow rate on the basis of a fluid dynamics model comprises a correcting of the at least one the flow velocity or the flow rate by simulating an outflow through said bifurcation using the fluid dynamics model.

7. The apparatus according to claim 3, wherein the computing the at least one of the flow velocity or flow rate on the basis of a fluid dynamics model comprises a correcting of the at least one of the flow velocity or flow rate by simulating a vessel friction between the first intravascular measurement position and the second intravascular measurement position using the fluid dynamics model.

8. The apparatus according to claim 1, wherein the intravascular pressure data comprises intravascular pullback data comprising a plurality of intravascular pressure values acquired in-situ using a pullback recording at a plurality of intravascular positions along a longitudinal axis of the vessel of interest;

wherein identifying the first intravascular measurement position and identifying the second intravascular measurement position comprise identifying, from the plurality of intravascular pressure values acquired at the plurality of intravascular positions, at least one intravascular pressure value exhibiting a localized change at one or more candidate position(s) from the plurality of intravascular positions;

wherein the one or more candidate position(s) is identified as the first intravascular measurement position and a further intravascular position other than the one or more candidate position(s) is identified as the second intravascular measurement position.

9. The apparatus according to claim 8, wherein identifying the first intravascular measurement position and identifying the second intravascular measurement position further comprise:

indicating the first intravascular measurement position and the second intravascular measurement position in the at least one diagnostic image.

10. The apparatus according to claim 1, wherein the vessel feature affecting at least one of the flow velocity or the flow rate is a bifurcation;

wherein the identification unit is further configured for:

selecting, if the bifurcation is present, at least one of: a third intravascular measurement position to replace the second intravascular measurement position.

11. The apparatus according to claim 10, wherein the identification unit is configured for: deriving a third intravascular pressure value using the intravascular pressure data obtained by the intravascular device at the second third intravascular measurement position;

wherein the computation unit is configured for computing at least one of a flow velocity or a flow rate in the vessel of interest based on the first intravascular pressure value at the first intravascular measurement position and the third intravascular pressure value at the third intravascular measurement position; and wherein the display unit configured for displaying a graphical representation of the at least one of the flow velocity or the flow rate.

12. A method for assessing a coronary vasculature comprising:

receiving intravascular pressure data of a vessel of interest in the vasculature of a patient obtained by an intravascular device at a plurality of measurement positions within the vessel of interest and at least one diagnostic image;

identifying, a first intravascular measurement position of the plurality of measurement positions;

deriving a first intravascular pressure value at the first intravascular measurement position, identifying a second intravascular measurement position of the plurality of measurement positions;

deriving a second intravascular pressure value at the second intravascular measurement position;

registering the at least one diagnostic image and the intravascular pressure data;

determining, based on the registration, if a vessel feature affecting at least one of a flow velocity or a flow rate in the vessel of interest is positioned between the first intravascular measurement position and the second intravascular measurement position;

computing, if no vessel feature is determined, at least one of the flow velocity or the flow rate in the vessel of interest based on the first intravascular pressure value at the first intravascular measurement position and the second intravascular pressure value at the second intravascular measurement position; and displaying a graphical representation of the at least one of the flow velocity or the flow rate.

13. The method according to claim 12, wherein the identifying the first intravascular measurement position and the second intravascular measurement position comprises indicating, to a user, the first intravascular measurement position and second intravascular measurement position.

14. A non-transitory computer-readable medium having stored thereon a computer program, wherein, when executed by a processing unit, the computer program is configured to cause the processing unit to perform the method of claim 12.

* * * * *